US010716884B2

(12) United States Patent
Weaver et al.

(10) Patent No.: US 10,716,884 B2
(45) Date of Patent: *Jul. 21, 2020

(54) ELECTRICAL SENSOR FOR FLUIDS

(71) Applicant: Fresenius Medical Care Holdings, Inc., Waltham, MA (US)

(72) Inventors: Colin Weaver, Pleasanton, CA (US); Elliott Alber, Pleasanton, CA (US); Philip Scott James, Orinda, CA (US); Daniel Schmidt, Petaluma, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/513,291

(22) Filed: Jul. 16, 2019

(65) Prior Publication Data

US 2019/0336666 A1 Nov. 7, 2019

Related U.S. Application Data

(63) Continuation of application No. 14/982,805, filed on Dec. 29, 2015, now Pat. No. 10,406,269.

(51) Int. Cl.
*A61M 1/16* (2006.01)
*G01N 27/07* (2006.01)

(52) U.S. Cl.
CPC ........ *A61M 1/1605* (2014.02); *A61M 1/1607* (2014.02); *A61M 1/1609* (2014.02); *A61M 1/1656* (2013.01); *A61M 1/1664* (2014.02); *A61M 1/1696* (2013.01); *G01N 27/07* (2013.01); *A61M 2205/0227* (2013.01);
(Continued)

(58) Field of Classification Search
None
See application file for complete search history.

(56) References Cited

U.S. PATENT DOCUMENTS 5,631,352 A 5/1997 Lauk
5,644,240 A 7/1997 Brugger
(Continued)

FOREIGN PATENT DOCUMENTS

CN 1430765 A 7/2003
CN 1650057 A 8/2005
(Continued)

OTHER PUBLICATIONS

U.S. Appl. No. 14/982,805, filed Dec. 29, 2015.
(Continued)

*Primary Examiner* — Richard C Gurtowski
(74) *Attorney, Agent, or Firm* — Leydig, Voit & Mayer, Ltd.

(57) ABSTRACT

An electrical sensor for sensing electromagnetic properties of process fluids in a dialysis machine or a similar medical device can include a probe for interfacing with the fluids that is made from electronic fabric materials. The electronic fabric probe can include one or more conductors embedded in a non-conductive fabric layer. The electronic fabric probe is accommodated an enclosure which establishes a flow path with respect to the probe to establish fluid contact between the process fluids and the conductors. The conductors can apply or sense current and/or voltage with respect to the fluid. A portion of the electronic fabric probe can be disposed externally of the enclosure to provide electronic communication externally of the enclosure.

18 Claims, 6 Drawing Sheets

(52) U.S. Cl.
CPC ............... *A61M 2205/3317* (2013.01); *A61M 2205/3331* (2013.01); *A61M 2205/3334* (2013.01); *A61M 2205/60* (2013.01)

(56) References Cited

U.S. PATENT DOCUMENTS

| | | | |
|---|---|---|---|
| 5,744,027 | A | 4/1998 | Connell et al. |
| 6,110,384 | A | 8/2000 | Goux et al. |
| 6,139,754 | A | 10/2000 | Hartranft et al. |
| 7,682,328 | B2 | 3/2010 | Han et al. |
| 7,794,141 | B2 | 9/2010 | Perry et al. |
| 7,891,243 | B2 | 2/2011 | Winkens |
| 7,896,831 | B2 | 3/2011 | Sternby et al. |
| 7,959,594 | B2 | 6/2011 | Wariar et al. |
| 8,246,567 | B2 | 8/2012 | Bene |
| 8,366,655 | B2 | 2/2013 | Kamen et al. |
| 8,708,946 | B2 | 4/2014 | Han et al. |
| 8,741,147 | B2 | 6/2014 | Bene et al. |
| 8,764,987 | B2 | 7/2014 | Gross et al. |
| 8,792,089 | B2 | 7/2014 | Zhang et al. |
| 8,801,646 | B2 | 8/2014 | Han et al. |
| 8,828,232 | B2 | 9/2014 | Shah et al. |
| 8,834,401 | B2 | 9/2014 | Petisce et al. |
| 8,870,769 | B2 | 10/2014 | Deshpande |
| 8,880,371 | B2 | 11/2014 | Beyer et al. |
| 8,889,004 | B2 | 11/2014 | Updyke et al. |
| 8,894,600 | B2 | 11/2014 | Kelly et al. |
| 8,900,172 | B2 | 12/2014 | Pohlmeier |
| 8,906,240 | B2 | 12/2014 | Crnkovich et al. |
| 8,973,424 | B2 | 3/2015 | Wiktor |
| 2003/0211797 | A1 | 11/2003 | Hill et al. |
| 2005/0082226 | A1 | 4/2005 | Bene et al. |
| 2005/0209563 | A1 | 9/2005 | Hopping et al. |
| 2007/0253463 | A1 | 11/2007 | Perry et al. |
| 2009/0007642 | A1 | 1/2009 | Busby et al. |
| 2011/0189048 | A1 | 8/2011 | Curtis et al. |
| 2012/0010554 | A1 | 1/2012 | Vantard et al. |
| 2012/0068723 | A1 | 3/2012 | Sullivan |
| 2012/0101422 | A1 | 4/2012 | Muller |
| 2012/0206239 | A1 | 8/2012 | Ikemoto |
| 2012/0232471 | A1 | 9/2012 | Chen et al. |
| 2012/0277552 | A1 | 11/2012 | Gerber |
| 2012/0277655 | A1 | 11/2012 | Gerber |
| 2013/0020237 | A1 | 1/2013 | Wilt et al. |
| 2013/0056419 | A1 | 3/2013 | Curtis |
| 2013/0131579 | A1 | 5/2013 | Mantell et al. |
| 2013/0319920 | A1 | 12/2013 | Hansson et al. |
| 2014/0060161 | A1 | 3/2014 | Schick et al. |
| 2014/0158538 | A1 | 6/2014 | Collier et al. |
| 2014/0158623 | A1 | 6/2014 | Pudil et al. |
| 2014/0190876 | A1 | 7/2014 | Meyer et al. |
| 2014/0190886 | A1 | 7/2014 | Pudil et al. |
| 2014/0190891 | A1 | 7/2014 | Lura et al. |
| 2014/0220699 | A1 | 8/2014 | Pudil et al. |
| 2014/0238909 | A1 | 8/2014 | Brugger et al. |
| 2014/0316297 | A1 | 10/2014 | McCaughan et al. |
| 2014/0326646 | A1 | 11/2014 | Strohhoefer et al. |
| 2015/0005699 | A1 | 1/2015 | Burbank et al. |
| 2015/0008183 | A1 | 1/2015 | Crnkovich et al. |
| 2015/0042366 | A1 | 2/2015 | Wilt et al. |
| 2015/0076044 | A1 | 3/2015 | Kelly et al. |
| 2015/0080782 | A1 | 3/2015 | Roger et al. |
| 2015/0088047 | A1 | 3/2015 | Gerber et al. |
| 2019/0056277 | A1 | 2/2019 | Ronay |
| 2019/0192022 | A1 | 6/2019 | Ram et al. |

FOREIGN PATENT DOCUMENTS

| | | |
|---|---|---|
| CN | 102316836 A | 1/2012 |
| CN | 104519846 | 4/2015 |
| WO | WO 2014/061777 A1 | 4/2014 |
| WO | WO 2015/011065 A1 | 1/2015 |

OTHER PUBLICATIONS

U.S. Appl. No. 16/081,033, filed Aug. 30, 2018.
"HealthPACT: Emerging Health Technology, An Overview of Emerging Home Renal Dialysis Technologies Including Nx Stage," Health Policy Advisory Committee on Technology, State of Queensland, Australia (Aug. 2012).
Sam, Ramin, "Hemodialysis: Diffusion and Ultrafiltration," *Austin J. of Nephrology and Hypertension*, 1(2) (2014).
U.S. Appl. No. 16/081,033, filed Dec. 29, 2016.
CN201680077163.7, First Office Action, dated Apr. 23, 2020.

ELECTRICAL SENSOR FOR FLUIDS

CROSS-REFERENCE TO RELATED APPLICATIONS

This patent application is a continuation of copending U.S. patent application Ser. No. 14/982,805, filed on Dec. 29, 2015, which is incorporated herein by reference in its entirety.

BACKGROUND OF THE DISCLOSURE

Hemodialysis is a medical procedure performed to treat patients suffering from renal failure, kidney problems or other related conditions in which the kidneys are unable to adequately remove impurities and waste products from the patient's blood. In the hemodialysis process, a dialysis system or dialysis machine removes blood from the patient's body and directs it through a filtration device referred to as a dialyzer that filters the cleaned blood for return to the patient. The filtration process is performed by directing a liquid solution, often referred to as a dialysate, through the dialyzer, and which is separated from the blood therein by a membrane so that waste products are drawn or diffuse into the dialysate. To facilitate treatment of different patients with different conditions, the composition of the dialysate may be adjusted or regulated by the dialysis machine during the dialysis process, for example, by introducing different additives to the solution to adjust its characteristics.

To facilitate the preparation and adjustment of the dialysate solution, various sensors and controls are incorporated into the dialysis machine to monitor the preparation process and the composition of the dialysate solution. Using these sensors and controls, the dialysis machine can be designed to automatically make adjustments during the dialysis treatment, or a health care technician monitoring the sensors and controls can make the necessary adjustments. The sensors and controls may therefore play a significant role during the dialysis treatment. However, because the dialysis process necessarily involves human biological substances, the sensors and controls must be incorporated into the dialysis machine in a manner to isolate them or to enable their cleansing and/or sterilization. The present disclosure is directed to supplementing and improving the operation and functionality of the sensors and controls associated with a dialysis machine or similar medical device.

BRIEF SUMMARY OF THE DISCLOSURE

The disclosure provides an electrical or electromechanical sensor for analyzing process fluids in a dialysis machine or similar medical device by measuring or sensing certain electromagnetic properties associated with the fluid. To directly interface with the fluid, the electrical or electromechanical sensor can utilize an electronic fabric probe having conductive properties that is made of a pliable, non-conductive fabric layer with one or more electrical conductors attached thereto in an exposed manner. The conductors may be attached to the fabric layer by weaving, stitching, carding, matting, or other appropriate methods. Electronic fabrics of this type may also be referred to as electronic textiles or smart fabrics. The electronic fabric probe can be cut or trimmed to shape and disposed inside a non-conductive enclosure that defines a fluid chamber. Process fluids can be directed into the fluid chamber to electrically contact the exposed conductors of the electronic fabric probe. Accordingly, voltage and/or current can be applied to the process fluid in the fluid chamber through use of the conductors in the electronic fabric probe. To establish electrical communication with the conductors, a portion of the electronic fabric probe can extend externally of the enclosure. In an embodiment, the enclosure can be formed of molded plastic or the like and can be readily disassembled to enable removal of the electronic fabric probe.

A possible advantage is the disclosure provides an electrical sensor that can detect electromagnetic properties such as, for example, the characteristics of an electromagnetic field, which are associated with a process fluid in a dialysis machine or similar device through the use of conductive electronic fabrics. The electronic fabric probe may be cut from a larger swath of the electronic fabric material thereby providing a unique manufacturing benefit associated with the disclosure. Another possible advantage is that because the enclosure can be made of a low cost molded plastic and readily disassembled, the electrical sensor can be readily removed from the dialysis machine and either discarded in its entirety, or the electronic fabric probe can be removed from the enclosure and replaced. This advantage can be readily appreciated given the electrical sensor's exposure to potentially biohazardous process fluids. These and other advantages will become apparent from the following detailed description and the accompanying drawings.

DETAILED DESCRIPTION

Figure 1:
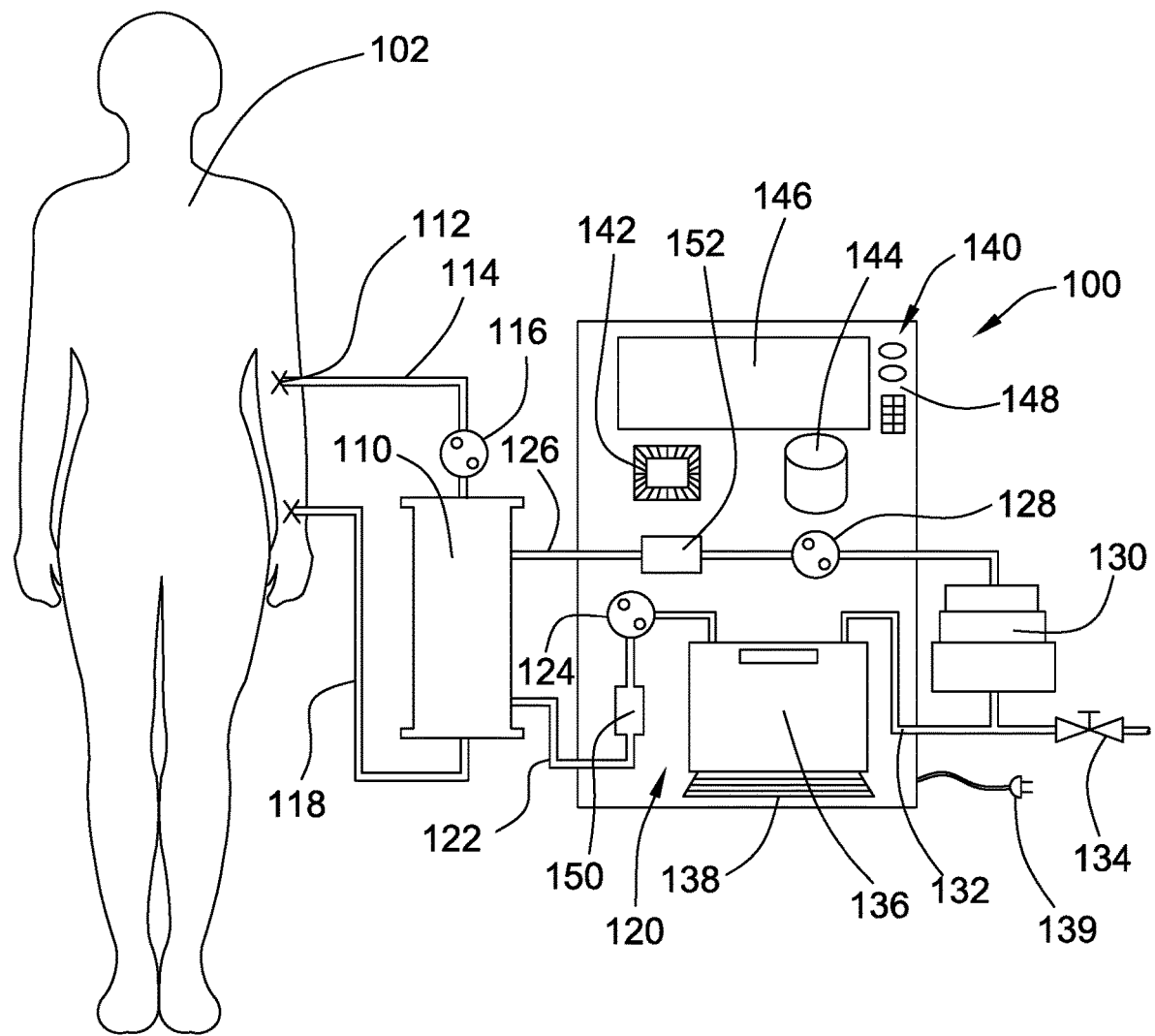
FIG. 1 is a front elevational schematic representation of a dialysis system for treating blood removed from a patient with dialysate fluid and that includes an electrical sensor for analysis of fluids utilized in the dialysis process.

Now referring to the drawings, wherein like reference numbers refer to like elements, there is illustrated in FIG. 1 a medical treatment system in the particular embodiment of a dialysis machine 100 for performing a hemodialysis treatment on a patient 102. It should be noted that although various aspects of the present disclosure are described with respect to hemodialysis treatment, these aspects may have application beyond hemodialysis treatment and are not intended to be specifically limited to hemodialysis, nor are the claims so limited unless explicitly stated. Furthermore, the illustrated dialysis machine may be intended for at-home use or portability outside of a medical clinic; however, aspects of the disclosure may be applicable to other configurations for dialysis treatment and the claims are not intended to be so limited unless explicitly stated therein. The dialysis machine 100 can be equipped with a dialyzer 110 in which the filtration of blood is performed. The dialyzer 110 can be a cross-flow dialyzer in which blood flowing in one direction is separated from a dialysate fluid flowing in the opposite direction by a semi-permeable membrane. During the dialysis process, solutes, fluids, and impurities in the blood can diffuse or transfer across the membrane to the dialysate to be directed out of the dialyzer 110. In various embodiments, the dialyzer 110 may be a single use device or may be configured for multiple uses.

To direct blood from the patient 102 to the dialyzer 110, a catheter 112 is inserted into the patient and can be connected to the dialysis machine 100 via tubing or a removal line 114. The catheter 112 may be temporarily inserted for the procedure or may be surgically grafted into the body of the patient 102. To maintain the flow of blood from the patient 102 to the dialyzer 110, a pump 116 such as a rotary peristaltic pump can be operatively associated with the dialyzer 110 and can be disposed along the removal line 114 to apply a pressure to the lines that directs or supplements blood flow in the appropriate direction. Filtered blood from the dialyzer 110 is returned to the patient 102 via a return line 118.

To supply dialysate during the dialysis treatment, the dialysis machine 100 can be operatively associated with a dialysate system 120 that is configured to prepare and adjust the dialysate solution. In an embodiment, the dialysate system 120 can be a sorbent system in which the dialysate is reformulated and re-circulated by the dialysis machine 100 without a significant production of waste fluid, although in other embodiments, the dialysis machine can be a more conventional single pass system in which used dialysate must be stored in a suitable receptacle for eventual disposal. To introduce fresh dialysate to the dialyzer 110, the dialyzer can be disposed in fluid communication with the dialysate system 120 through a dialysate supply line 122, which may be a flexible hose or tubing of appropriate, medically suitable material. Disposed in line with the dialysate supply line 122 can be another peristaltic pump 124 that applies appropriate pressure to direct the dialysate solution through the dialyzer 110. After passing through the dialyzer 110 to treat the counter flowing blood, the used dialysate is returned to the dialysis machine 110 by a dialysate return line 126, which may be associated with a third peristaltic pump 128 to maintain flow of the dialysate solution.

To facilitate recycling and reconditioning of the used dialysate, the dialysate solution is directed by the dialysate return line 126 to a sorbent cartridge 130 where the fluid is cleaned and purified. The sorbent cartridge 130 can be a disposable unit made of a plurality of layers or segments of different elements and compounds that trap and remove impurities in the dialysate solution that were disposed therein from the blood during the dialysis process. The impurities remain in the sorbent cartridge 130 while the filtered dialysate is returned to the dialysis machine 100 via a sorbent return line 132. An advantage of the sorbent system is that it recycles much of the dialysate solution, including the purified reverse osmosis water initially utilized for the dialysate, while providing a convenient manner for disposing of the biological impurities removed from the patient's blood through the dialyzer 110. However, in various embodiments, the sorbent return line 132 can be in fluid communication with a reverse osmosis water supply 134 that can supplement the water content of the recycled solution if necessary.

To further recondition the solution returned from the sorbent cartridge 130, the dialysate system 120 can include a cassette or dialysate bag 136 disposed in the dialysis machine and which contains various additives and chemicals. The dialysate bag 136 may also include tubing or flow channels for directing the recycled solution into contact with the additives for incorporation and may further be compartmentalized to separate the additives. To facilitate adsorption of the additives into the recycled solution and to avoid cooling of the patient blood during the dialysis process, the dialysate bag 136 may be operatively associated with a heater 138. The quantities of the additives may be measured and intended for a single dialysis treatment process or, in other embodiments, they may be added to the recycled solution via appropriate metering equipment. In the single use embodiment, the dialysate bag 136 can be removed from the dialysis machine and replaced after use. In addition to the dialysate bag 136, the dialysate system 120 can include other sources of compounds and fluid solutions to formulate the dialysate and may be associated with meters and detectors to check for blood presence in the dialysate, quality levels, composition and formulation of the dialysate, may include de-aerators, etc. The freshly prepared dialysate is directed again to the dialyzer by the dialysate supply line 122. To provide electrical power for operation of the peristaltic pumps 124, 128 and the heater 138 as well as other equipment, the dialysis machine 100 can be operatively associated with a power source 139, such as a plug for an electrical outlet or, in other embodiments, a rechargeable battery pack.

To monitor and control the dialysis process, an electronic or computerized control unit, module, or controller 140 can be operatively associated with the dialysis machine 100. The controller 140 is adapted to monitor various operating parameters and to responsively regulate various variables and functions affecting the dialysate system 120 and the other systems of the dialysis machine 100. The controller 140 can include a microprocessor 142, an application specific integrated circuit (ASIC), or other appropriate circuitry, and can have memory 144 or other data storage capabilities on a computer readable medium. The microprocessor 142 and the memory 144 can be configured to store, retrieve, and execute programming instructions to conduct the dialysate formation and recycling process and adjustably respond to changes in the process as they arise. To enable a technician or operator to interface with the dialysis machine, the controller 140 can be operatively associated with a human-machine interface 146 such as a liquid crystal display device that may include touch screen capabilities. The human-machine interface 146 can display visual information regarding the dialysis process and the operational state of the dialysis machine 100 and can receive input from the operator through tactile capabilities. The controller 140 may be further associated with a physical control panel 148 that includes switches, knobs, keypads, and the like through which the operator may initiate and adjust the dialysis processes.

To monitor and analyze the composition, parameters, and characteristics of the fluid solutions processed by the dialysate system 120, the dialysis machine 100 can include various sensors, particularly electrical sensors, disposed in fluid communication with the system. The sensors may be electrically or electronically actuated and may work on electromagnetic principals to analyze and measure information regarding the fluids that are important to the dialysis process. Measured parameters may include conductivity, temperature, flow rate, pH level, and other characteristics. For example, to analyze and determine the composition and quality of the recycled dialysate before directing it to the dialyzer 110, the dialysis machine 100 can include a supply sensor 150 disposed in the dialysate supply line 122 just upstream of the dialyzer. In addition, to receive and determine the quality and composition of the used dialysate returning from the dialyzer 110 after treatment of the patient's blood, a return sensor 150 can be disposed in the dialysate return line 126 downstream of the dialyzer. The supply and return sensors 150, 152 can also be in electrical communication with the controller 140 to send and receive information between the components. Communication can be established by sending and receiving non-transitory analog or digital signals over communication busses such as conductive wires, optical waveguides, and the like disposed through the dialysis machine 100. Additional electrical sensors can be incorporated at other locations within the dialysate system 120 to monitor other fluid properties.

To analyze the dialysate of the dialysis machine or other process fluids of similar medical devices, the electrical sensors can be placed in direct fluidic contact with the subject fluid and may include electrical or electronic components disposed to assess electrical or magnetic properties of the fluids. For example, in an embodiment, the electrical sensor can be a conductivity sensor that measures electrical conductivity of the subject fluid. Most liquids have the ability to conduct or pass an electrical current to a degree. The electrical charge is carried by electrolytes or ions, including cations (positive) and anions (negative), present in the fluid. The number of ions in the fluid, and thus the ability of the fluid to conduct or resist electric current, is dependent upon a number of factors including the composition of the fluid, temperature, flow rate, and volume. If factors such as volume and temperature are known and accounted for, then the measurable conductivity of the fluid can be used to deduce the unknown composition of the fluid.

To measure the conductivity of a fluid, the electrical sensor is configured to apply a current or voltage to a volume of the fluid between two predetermined points or locations. The resistivity of the fluid to passing electricity, which is the mathematic reciprocal of conductivity, causes a drop or decrease in the voltage and/or current between the two points. An appropriate electrical meter can measure the decrease in those parameters which are reflective of the fluid's resistivity and thereby establish the conductivity of the fluid by the mathematical relation. The physical and electrical coupling between the electrical sensor and the fluid occurs in a device or unit referred to as a conductivity cell that includes electrodes to apply and sense the voltage and/or current.

Figure 2:
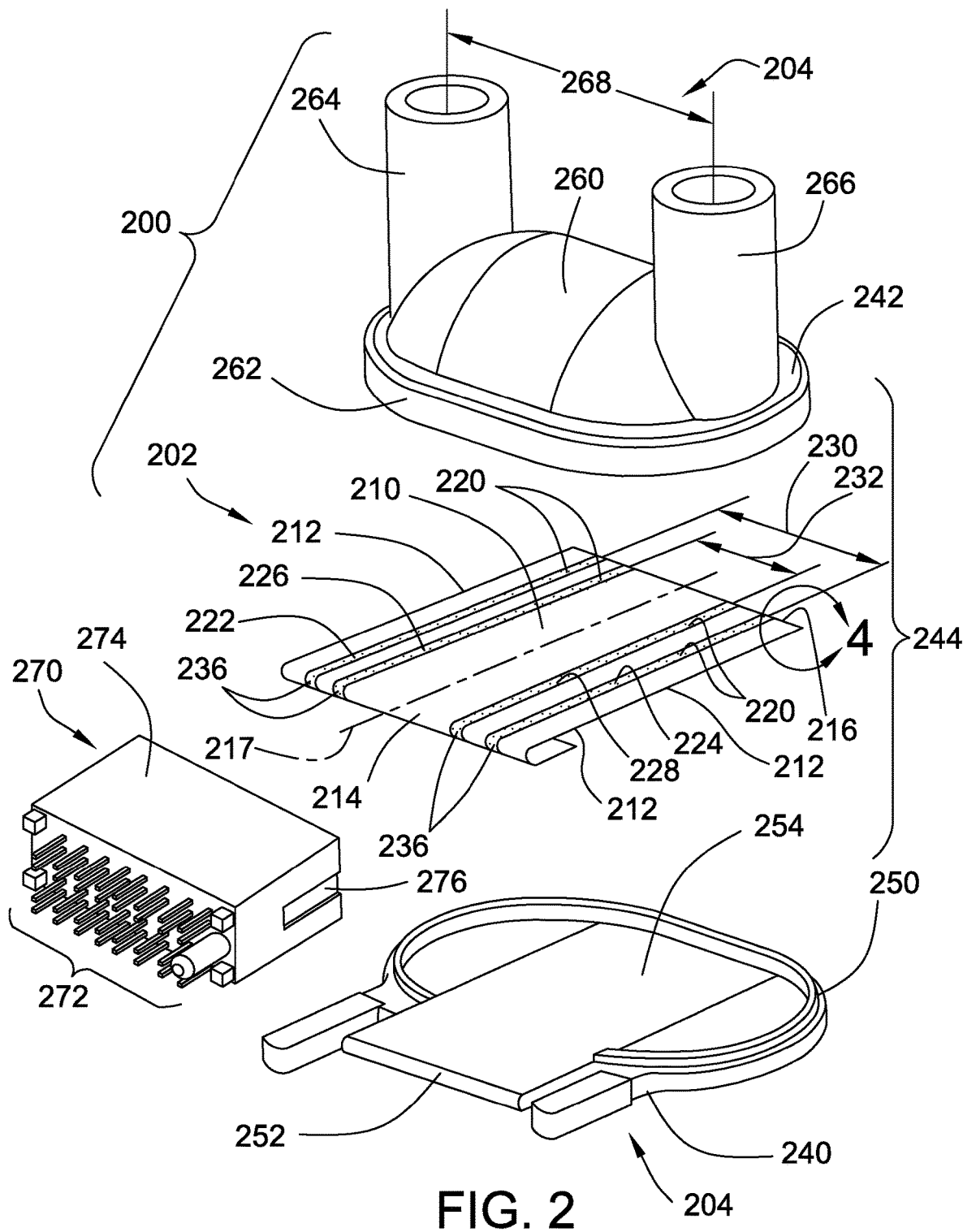
FIG. 2 is an exploded view of one embodiment of the electrical sensor for the dialysis system which utilizes a four-conductor electronic fabric probe disposed in a housing having a flow-over configuration.
Figure 3:
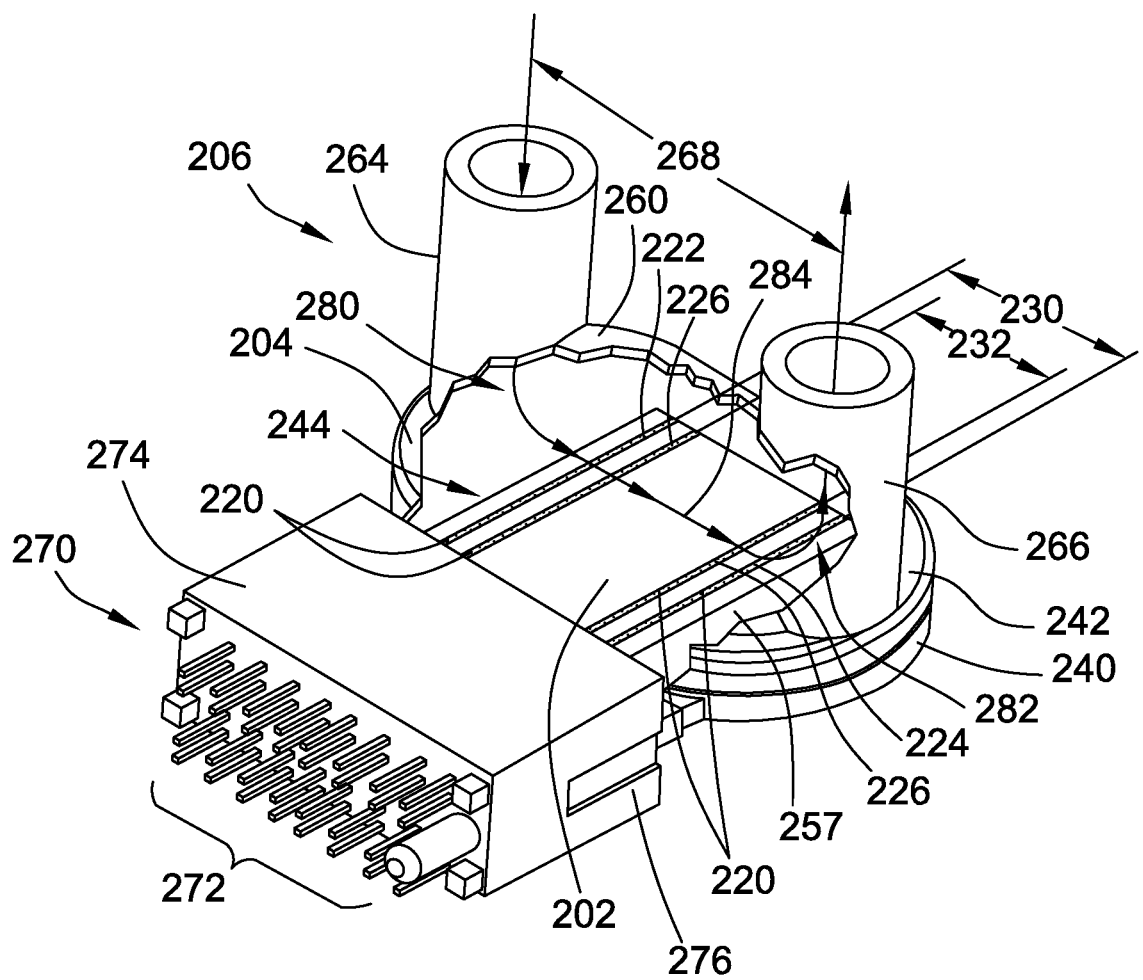
FIG. 3 is a partially cutaway, perspective assembly view of the embodiment of FIG. 2 illustrating the fluid flow through the electrical sensor across the electronic fabric probe.

Referring to FIGS. 2 and 3, there is illustrated an embodiment of an electrical sensor 200 configured to establish fluid communication with the process fluid of a dialysis machine or similar medical device and that includes electrical components such as conductive elements disposed in physical contact with the fluid and thereby function as a conductivity cell. In particular, the electrical sensor 200 includes a probe 202 made from a piece of electronic fabric material having one or more conductive electrodes embedded therein that can be accommodated in a non-conductive housing or enclosure 204 to establish a fluid path across the electronic fabric probe 202. Electronic fabrics or electronic textiles are a class of materials in which electronic components are disposed in fabric-like materials or sheet-like materials, non-conductive in character, and are intended for similar applications as traditional fabrics and textiles. Examples include wearable electronics. A characteristic of electronic fabrics is their flexible, sheet-like structure enables them to cover and conform to a surface. In accordance with an aspect of the disclosure, the electronic fabric probe 202 can be cut or trimmed from a larger swath of electronic fabric material for its specific application in the electrical sensor, thereby facilitating manufacturability of the probes. For example, various sizes and shapes can be cut from the same swath of electronic fabric.

Figure 4:
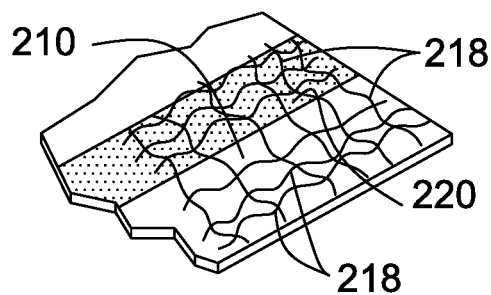
FIG. 4 is a detailed perspective view of the area indicated in FIG. 2 illustrating structural details of an embodiment of the electronic fabric probe.

In the embodiment illustrated in FIGS. 2 and 4, the electronic fabric probe 202 includes a non-conductive fabric layer 210 that may have a planar, polygonal shape delineating a rectangular outline or peripheral edge 212. The polygonal shape further provides a first side edge 214 and a parallel, spaced apart second side edge 216 that extend perpendicular to a centerline 217 of the fabric layer 210. The fabric layer 210 also has a pliable, sheet-like characteristic or property and may be composed of individual fibers 218 or threads of natural or synthetic materials that have been assembled together in an interlocking manner such as by, for example, weaving, knitting, sewing, carding, bonding, matting, pressing, etc. Alternatively, the non-conductive fabric layer 210 can be made from flexible, thinly formed, plastic films. In an embodiment, the non-conductive material for the fabric layer can be made from polyethylene Terephtharlate (PET) mesh. The fabric layer 210 can have some fluid permeability or porosity to facilitate its interaction with the process fluids of the medical device. The thickness of the sheet-like fabric layer 210 and its permeability can be selected based on the application and fluid flow to be encountered.

To provide electrodes for the electronic fabric probe 202, one or more conductors 220, and up to any suitable number of conductors, can be disposed on the fabric layer 210. In the illustrated embodiment, the conductors 220 can be made of thin strips of conductive material woven, stitched, or otherwise embedded into the non-conductive fabric layer 210 in such a manner that at least a portion of the conductor is exposed along a surface of the fabric layer. More specifically, the conductors 220 can be long, thin rectangular threads arranged on the fabric layer to facilitate their electromagnetic utility. Suitable materials for the conductors 220 include stainless steel, aluminum, gold, copper, etc., and the conductors 220 can be stamped from thin metallic sheets or foil, although in other embodiments the conductors can be formed as thin-gauged wires. As illustrated in FIG. 4, in an embodiment, the conductor may be secured to the fabric layer 210 by random fibers extending across the width of the conductors.

Various types of conductivity sensors are available and may include any suitable number of conductors for making selected measurements. For example, in the embodiment illustrated in FIG. 2, the electronic fabric probe 202 can be configured as a four-electrode device and can include a first conductor 222, a second conductor 224, a third conductor 226, and a fourth conductor 228. The first, second, third, and four conductors 222, 224, 226, 228, extend lengthwise between the first side edge 214 and the second side edge 216 of the non-conductive fabric layer and are arranged parallel to and spaced apart from each other with respect to the centerline 217. Further, the first and second conductors 222, 224 can be directed outwardly toward the peripheral edges 212 by a given first distance 230 with respect to the centerline 217 while the third and fourth conductors 226, 228 are directed inwardly of the first and second conductors and spaced apart a second distance 232 that is less than the first distance. The first and second distances 230, 232 are generally maintainable because the conductors 220 are embedded in the fabric layer 210 by stitching, weaving, etc. The terminal ends of the four conductors along the first side edge 214 can form a respective plurality of leads or terminals 236 for the electronic fabric probe 202.

To accommodate the electronic fabric probe 202, the enclosure 204 illustrated in FIG. 2 can be configured as a two-piece construction having a first enclosure portion 240 and a second enclosure portion 242 that, when assembled together, can delineate an enclosed fluid chamber 244. The first enclosure portion 240 can be a lower portion formed as a flat, planar structure having an oblong or oval shape delineating an oval-shaped outline 250. Projecting from one side of the oval-shaped outline 150 can be a connector tongue 252, the utility of which is described more fully below. Disposed into a surface of the flat first enclosure portion 240 can be a slight depression 254 extending along the connector tongue 252 toward the opposite edge of the oval-shaped outline 150. The width of the depression 254 can correspond generally to the width of the fabric layer 210 measured perpendicularly to the centerline 217. Accordingly, in the present embodiment, the electronic fabric probe 202 can be placed in the depression 254 adjacent the planar surface of the first enclosure portion 240 when the first enclosure portion is assembled to the second enclosure portion 242. When so assembled, the first side edge 214 of the fabric layer 210 can align along the connector tongue 252 where the terminals 236 of the conductors 220 can be exposed externally of the enclosure 204.

To create the fluid chamber 244, the second enclosure portion 242 can be formed as a hollow dome 260 extending upwardly from an oval-shaped base 262 that corresponds to the oval-shaped outline 250 of the lower enclosure portion 240. The dome 260 can delineate a hollow cavity underneath that corresponds generally to the fluid chamber 244. The cross-sectional area and/or the volume of the fluid chamber 244 can be predetermined by the shape of the dome 260, which may be advantageous for reasons explained below. To connect the electrical sensor 200 to the tubes or hosing of the dialysate system, the second enclosure portion 242 includes an upwardly extending fluid inlet 264 and a corresponding fluid outlet 266 that may be configured as cylindrical hose fittings. Connection may be established by press-fitting, hose clamps, etc. The fluid inlet 264 and the fluid outlet 266 are parallel to and spaced apart from each other toward opposite ends of the oval-shaped base 262 by a third distance 268 that may be larger than either the first or second distances 230, 232 associated with the fabric layer 210. The first enclosure portion 240 and the second enclosure portion 242 can be made of any suitable non-conductive material including, for example, molded polycarbonate. The first and second enclosure portions 240, 242 can be joined together, in a snap-fit relation, by clamps, etc. such that the enclosure 404 can be readily assembled and disassembled.

To establish electronic communication with the conductors 220 on the electronic fabric probe 202 when accommodated in the assembled enclosure 204, the electrical sensor 200 can be operatively associated with an attachable electrical connector 270. The electrical connector 270 can be in the form of a pin header having a plurality of conductive leads or pins 272 arranged in and projecting from an insulative box or shroud 274. The electrical connector can further include a slot 276 disposed in the shroud 274, opposite the side from where the pins 272 project, that enables the connector to receive and attach to the connector tongue 252 extending from the lower enclosure housing 240. Accordingly, a portion of the pins 272 can make electrical contact with the terminals 236 of the conductors 220 along the first side edge 214 of the fabric layer 210. When the electrical sensor 200 is disposed in the dialysis machine or similar medical device, the electrical connector 270 can mate with a corresponding receptacle in the device to establish electrical communication between the electrical sensor 200 and a controller of the dialysis machine or similar device.

The flow of process fluids through the electrical sensor 200 and the conductivity measurements obtained can be described with respect to FIG. 3. In particular, separate areas of the fluid chamber 244 can be further designated as an entry region 280 corresponding to the fluid inlet 264 and disposed toward one end of the oblong-shaped enclosure 204 and an exit region 282 corresponding to the fluid outlet 266 and disposed toward the opposite end of the enclosure. The electronic fabric probe 202 adjacent the lower first enclosure portion 240 is exposed to the fluid chamber 244 with its upper surface directed toward the fluid inlet 264 and fluid outlet 266. Fluid flowing inwardly into the entry region 280 and perpendicular to the lower enclosure portion 240 will accordingly be redirected horizontally along a fluid flow path 284 to the exit region 282 at the opposite end of the oblong enclosure 204. Further, the flow path 284 is generally perpendicular to and leads across each of the conductors 220 embedded in the electronic fabric probe 202 with each of the conductors traversing the flow path. Preferably, because the electronic fabric probe 202 is disposed in the depression 254 formed in the lower first enclosure portion 240, the position of the probe will be maintained as fluid is directed between the fluid inlet 264 and the fluid outlet 266. Further, because the conductors 220 are stitched or woven into the fabric layer, their relative positions with respect to each other are generally fixed at the predetermined first distance 230 and the predetermined second distance 232. The exposure of the conductors on the fabric layer and the fluid permeability associated with the fabric layer facilities electrical connection between the conductors and the process fluids.

In a four-electrode conductivity cell, two outer electrodes, corresponding here to the first conductor 222 and the second conductor 224, can be designated excitation electrodes. The excitation electrodes are coupled to a power source to apply a voltage or current between the first and second conductors 222, 224 causing a current to be conducted through the fluid in the internal chamber 244. The power source may supply either alternating current (AC) or direct current (DC) electricity. Because the process fluids are typically imperfect conductors, the fluid will cause a voltage drop between the first and second conductors 222, 224. The value of the voltage drop corresponds to the composition of the fluid, such as the presence or absence of ions, impurities, etc. To measure the voltage drop, the inner two electrodes, corresponding to the third and fourth conductors 226, 228, can be designated sense electrodes, or ground guards. The sense electrodes can be coupled to an appropriate meter such as an amp meter, an ohm meter, or preferably a voltage meter that senses the voltage drop between at least the third and fourth conductors 226, 228. The meter in turn can be coupled to or part of a controller such as described above to perform the following calculations. The measured voltage drop can be converted to the electrical resistance provided by the fluid between the sense electrodes according to Ohm's law:

$$\text{Ohm's Law: } V = I/R \tag{1}$$

Wherein V is the voltage drop, in volts;

I is the current, in amps or milliamps; and

R is the resistance, in ohms or milliohms.

Because the second distance 232 between the third and fourth conductors 226, 228, i.e., the sense electrodes, is predetermined by the arrangement of the electronic fabric probe 202, the calculated electrical resistance in ohms between the third and fourth conductors can be converted to the resistivity of the fluid. Resistivity is an intrinsic property of the fluid that quantifies how strongly it will oppose the flow of current and is typically presented in units of ohm*centimeters ($\Omega$*cm). Resistivity can be approximated by calculating the product of the measured and calculated resistance in ohms and the predetermined cross-sectional area A of the interior chamber 244 in cm$^2$, and dividing that value by L, the second distance 232 in cm:

$$\rho = R*A/L \qquad (2)$$

Because conductivity is the mathematical inverse of resistivity, the conductivity of the fluid flowing in the electrical sensor 200 is readily determined. Once the conductivity for the process fluid is calculated, it can be compared to empirically predetermined values to determine the composition or content of the process fluid, which provides discernible information about the dialysis process and indications on how it may be adjusted. The relationship between the above formulas and the characteristics of the process fluids may not be precisely linear or directly proportional, however, and may require calibration or estimation of calculated and determined values.

According to one advantageous embodiment, all or part of the electrical sensor 200 can be disposable. In particular, because the enclosure 204 connects to the fluid circuitry of the dialysis machine via hoses, the electrical sensor 200 can be readily removed from the dialysis machine during a cleansing process after use. Further, because the enclosure 204 can be readily disassembled into the separate first and second enclosure portions 240, 242, the electronic fabric probe 202 can be removed and discarded after use. The first and second enclosure portions 240, 242 can be sterilized and reused with a new electronic fabric probe 202 installed, or the entire electrical sensor can be discarded. Because the electrical sensor 200 necessarily contacts dialysate and other process fluids, the disposable aspect of all or part of the sensor improves its utility in medical and biological applications such as dialysis treatments.

Figure 5:
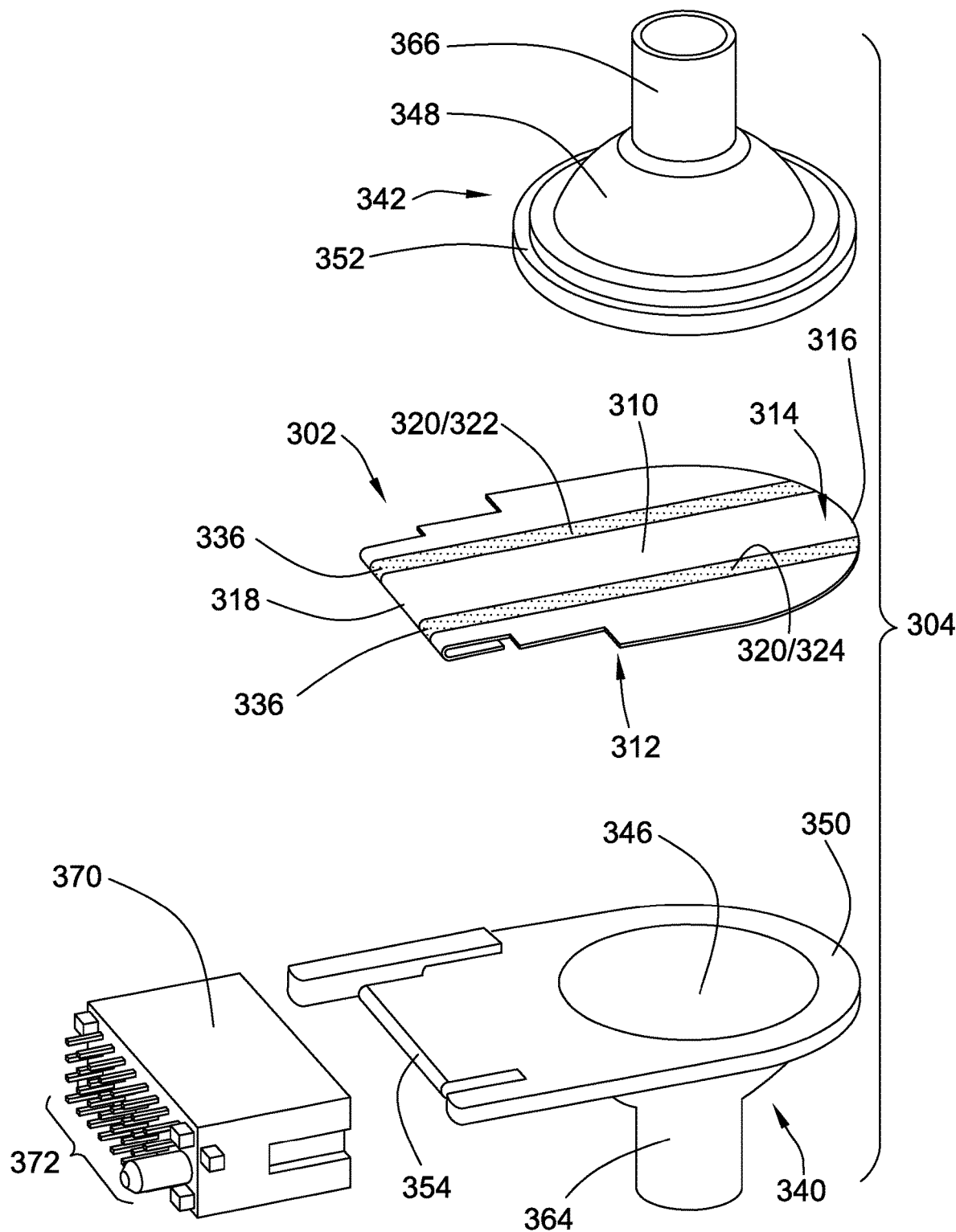
FIG. 5 is an exploded view of another embodiment of the electrical sensor that utilizes a two-conductor electronic fabric probe disposed in a housing having a flow-through configuration.
Figure 6:
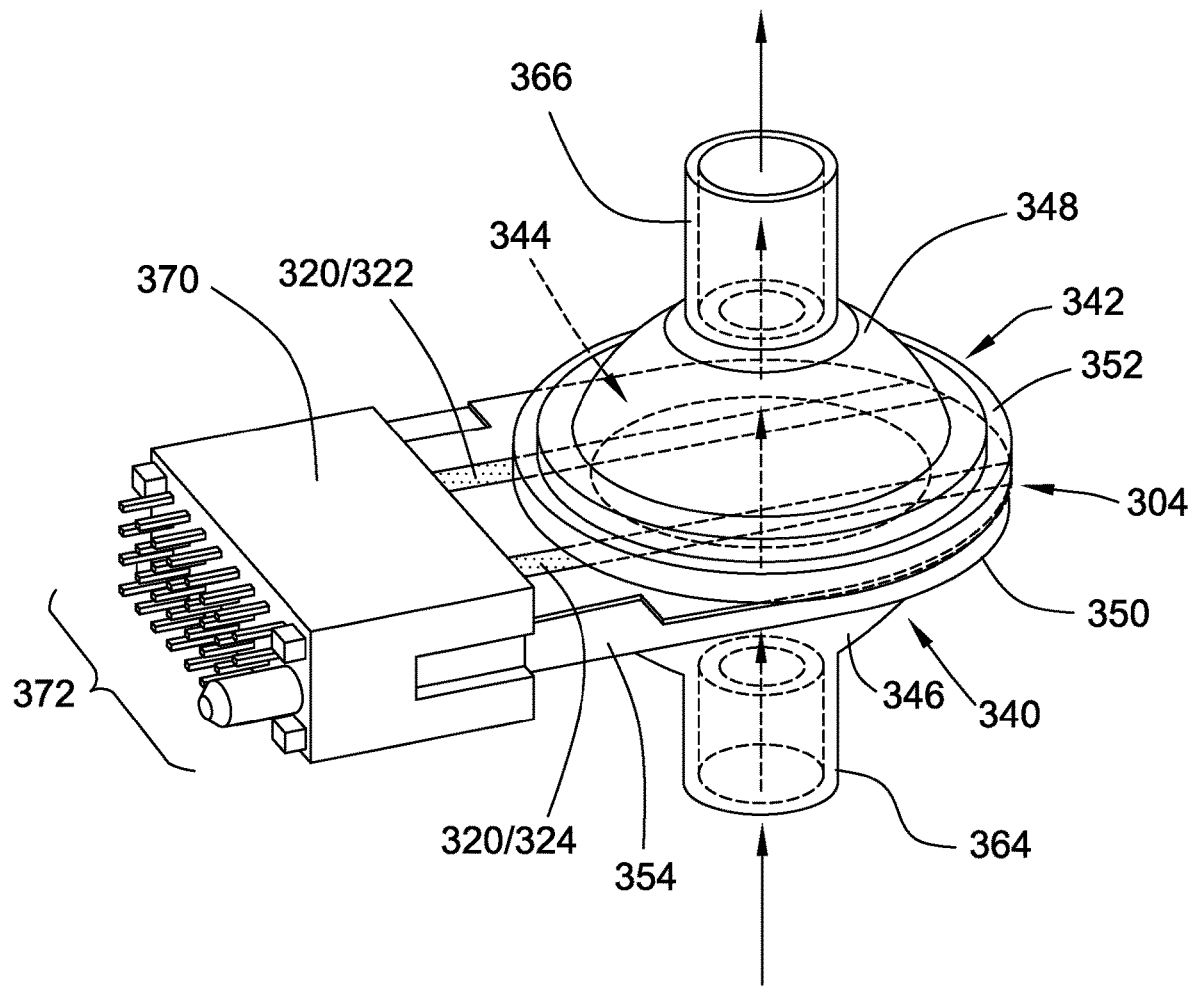
FIG. 6 is a perspective assembly view of the embodiment of FIG. 5 illustrating fluid flow through the electrical sensor, with the enclosed elements represented in dashed lines.

While the embodiment of the electronic fabric probe illustrated in FIGS. 2 and 4 has a four-electrode configuration, other configurations for the probe are possible including, for example, a two-electrode embodiment and a three-electrode embodiment. In addition, configurations other than the flow-over configuration are possible. Referring to FIGS. 5 and 6, there is illustrated a two-electrode, flow-through configuration for the electrical sensor 300 to analyze fluids in a dialysis machine or similar medical device. The electrical sensor 300 includes an electronic fabric probe 302 that can be accommodated in a two piece, non-conductive enclosure 304 configured to direct process fluids through the fabric probe. The electronic fabric probe 302 can be similar in construction to the probe described above and can include a flexible, planar fabric layer 310 with a plurality of conductors 320 disposed in it. To enable fluid to permeate through the fabric layer 302 from a first surface 312 to a second surface 314, the fabric layer 310 may be relatively porous or made from loosely woven, knitted, or matted fibers. Moreover, in the present embodiment, the fabric layer 310 can have a tongue-shaped outline including a curved peripheral edge 316 and a square or rectangular extension 318.

To function as the electrodes, the electronic fabric probe 302 can include a plurality of conductors 320 including a first conductor 322 and a second conductor 324 embedded in the fabric layer 310. The first conductor 322 and the second conductor 324 can be relatively thin, elongated strips of conductive material and can extend, parallel and spaced apart, lengthwise across the fabric layer 310 from the curved peripheral edge 316 to the rectangular extension 318. The first and second conductors 322, 324 can form terminals 336 where they terminate at the edge of the rectangular extension 318.

To accommodate the electronic fabric sensor 302 in a flow-through configuration, the enclosure 304 has a two-piece construction including a first or lower enclosure portion 340 and a second or upper enclosure portion 342 that can be assembled together to delineate an fluid chamber 344. In the illustrated embodiment, the lower enclosure portion 340 and the upper enclosure portion 342 can each have a respective hemispherical shaped dome 346, 348 that delineates a correspondingly hemispherical shaped cavity. It should be noted, however, that terms like "lower," "upper," "down," and "up" are for reference only and should not be construed as a limitation on the claims unless explicitly stated. The hemispherical domes 346, 348 can be of the same general dimensions. When assembled together, the first and second hemispherical domes 346, 348 provide the chamber 344 with a spherical shape. The lower and upper hemispherical domes 346, 348 can also include respective circular bases 350, 352 of corresponding diameters that mate together as flanges when the lower and upper enclosure portions 342, 344 are assembled. Extending perpendicularly from the circular base 350 of the lower enclosure portion 340 can be a flat, planar connector extension 354 corresponding to the rectangular extension 318 of the electronic fabric conductor 302.

When the electrical connector 300 is assembled, the electronic fabric conductor 302 is suspended in the spherical chamber 344 with the first surface 312 directed toward the lower hemispherical dome 346 and the second surface 314 directed upwardly toward the upper hemispherical dome 348. The curved peripheral edge 316 of the electronic fabric conductor 302 can be sandwiched between the first and second circular bases 350, 352. To direct fluid across the spherical chamber 344 and through the electronic fabric conductor 302, the lower enclosure portion 340 can include a downwardly directed fluid inlet 364 and the upper portion 342 can include an oppositely directed, upward fluid outlet 364. The oppositely disposed fluid inlet 364 and fluid outlet 366 delineate a fluid flow path 368 similar to an axis line disposed across the spherical fluid chamber 344. Process fluid introduced to the electrical sensor 300 through the fluid inlet 364 must permeate and traverse across the electronic fabric sensor 302 to reach the fluid outlet 366. If a power source is applied to the first conductor 322 designating it an excitation electrode, current will be conducted through the fluid across the electronic fabric probe 302 to the second conductor 324 that functions as a sense electrode. To establish electrical communication with the first and second conductors 322, 324 to apply and sense voltage and/or current, an electrical connector 370 including a plurality of conductive pins 372 can be attached to the connector extension 354 of the lower enclosure portion 340.

Figure 7:
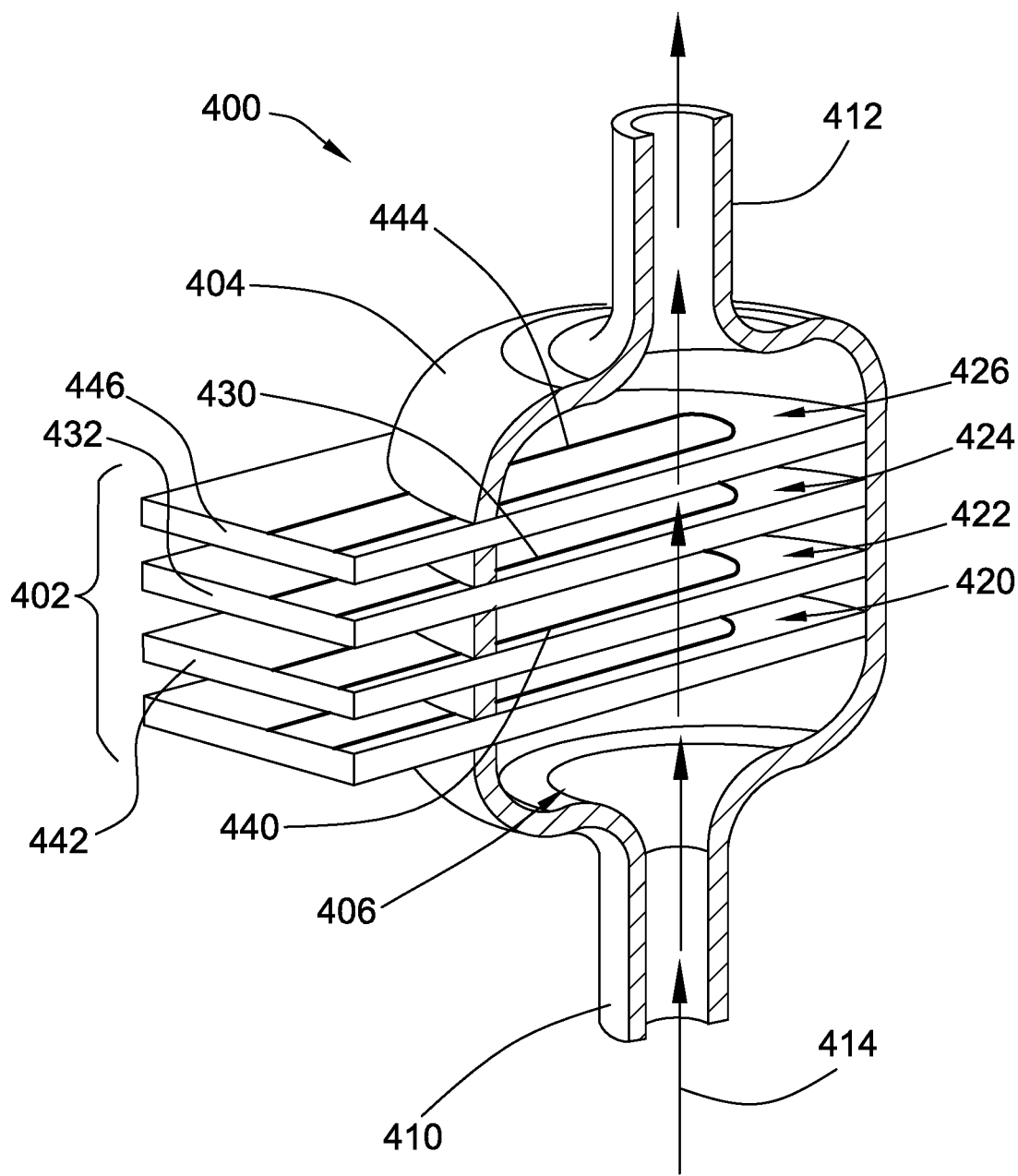
FIG. 7 is a partially cutaway perspective view of another embodiment of the electrical sensor that utilizes a plurality of electronic fabric probes for analyzing different aspects of the fluid utilized in the dialysis process.

In addition to measuring conductivity of a process fluid, electrical sensors of the foregoing type can be configured to measure other parameters and characteristics of the fluids processed through a medical device such as a dialysis machine. Referring to FIG. 7, there is illustrated an embodiment of an electrical sensor 400 having a plurality of electronic fabric probes 402 arranged to measure flow rate through the sensor in addition to conductivity. The plurality electronic fabric probes 402 are accommodated in a non-conductive enclosure 404 that defines an internal fluid chamber 406 in which the probes are suspended. The enclosure 404 is generally drum shaped so the fluid chamber 406 delineates a heightened cylinder in which the electronic fabric probes 402 are vertically disposed. To establish a flow-through configuration for the electrical sensor 400, the enclosure 404 can have a downward fluid inlet 410 and an oppositely directed upward fluid outlet 412 that delineate a flow path 414 through the probes 402 and across the fluid chamber 406. Portions of the electronic fabric probes 402 protrude radially outward from a side of the enclosure 404 for connecting with associated equipment.

The first electronic fabric probe 420, disposed lowest in the fluid chamber 406, can measure the conductivity of the process fluid and can have any of the foregoing configurations. The second, third, and fourth electronic fabric probes 422, 424, and 426 can be arranged to determine flow rate through the fluid chamber 406 by sensing temperature differences in the fluid. In particular, the third electronic fabric probe 424 may be a heating probe and may include one or more heating conductors 430, in the structural form of metallic wires or threads, embedded in the non-conductive fabric layer 432 of the third electronic fabric probe. The heating conductors 430 may have a sufficient electrical resistance causing them to heat when a current is applied to the third electronic fabric probe 424. The heating conductors 430 can transfer the generated heat to the fluid flowing through the third electronic fabric probe 424. The second and fourth electronic fabric probes 422, 426, arranged above and below the third electronic fabric probe 424, can be configured as thermal sensing probes. For example, the second electronic fabric probe 422 can include a first sensing conductor 440 embedded in the respective fabric layer 442 that is formed as a closed loop or circuit leading into and out of the fluid chamber 406. The electrical resistance associated with the first sensing conductor 440 can be proportionally dependent upon temperature and changes according to an increase and decrease in the temperature of the surrounding environment. The fourth electronic fabric probe 426 can include a similarly arranged second sensing conductor 444 embedded in the respect fourth fabric layer 446.

In operation, as the process fluid from the fluid inlet 410 flows along the flow path 414 and permeates through the second electronic fabric conductor 422, a meter operatively associated with the first sensing conductor 440 can determine its resistance by measuring the voltage drop over the first sensing conductor. The process fluid next permeates the third electronic fabric probe 424 where the heating conductor 430 can transfer generated heat to the fluid flowing past it. The second sensing conductor 444 disposed in the fourth electronic fabric probe 426 can also be operatively associated with a meter that determines the resistance of the second sensing conductor by measuring the associated voltage drop. The resistance measurements between the first sensing conductor 440 and the second sensing conductor 444 can be compared to determine the temperature difference between the second electronic fabric probes 422 and the fourth electronic fabric probes 426. If the heat energy input through the heating conductor 430 is known, the flow rate of process fluid through the fluid chamber 406 is readily solvable. In further embodiments, the electrical sensor can measure other qualities and parameters such as temperature.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An electrical sensor for a medical machine comprising:
 a fluid chamber comprising a fluid inlet and a fluid outlet, wherein the fluid chamber is configured for fluid to flow in a flow path from the fluid inlet to the fluid outlet;
 an electrical fabric probe disposed within the fluid chamber, the electrical fabric probe comprising non-conductive fabric material and a plurality of conductive strips embedded in the non-conductive fabric material, wherein the plurality of conductive strips are configured for measuring a parameter of the fluid while immersed in the fluid; and
 an electrical connector configured to connect the plurality of conductive strips within the fluid chamber to an electronic controller outside the fluid chamber.

2. The electrical sensor of claim 1, wherein the non-conductive fabric material is formed as a non-conductive mesh and the plurality of conductive strips are formed as conductive threads embedded in the non-conductive mesh.

3. The electrical sensor of claim 1, wherein the parameter of the fluid correlates to conductivity of the fluid flowing in the flow path.

4. The electrical sensor of claim 1, wherein the parameter of the fluid measured by the plurality of conductive strips is a voltage drop corresponding to the fluid, and wherein the electronic controller is configured to use the voltage drop to determine a resistivity and/or a conductivity of the fluid.

5. The electrical sensor of claim 1, wherein the fluid inlet and the fluid outlet are configured as hose fittings, and wherein the electrical sensor is removable from the medical machine.

6. The electrical sensor of claim 1, wherein the fluid chamber comprises a first portion and a second portion which are configured to be disassembled to facilitate removal and replacement of the electrical fabric probe disposed within the fluid chamber.

7. The electrical sensor of claim 1, further comprising:
a plurality of additional electrical fabric probes disposed within the fluid chamber, wherein the plurality of additional electrical fabric probes include second and fourth electrical fabric probes configured to sense temperature and a third electrical fabric probe configured to heat the fluid flowing in the flow path;
wherein the electronic controller is configured to determine a flow rate of the fluid based on a temperature difference sensed by the second and fourth electrical fabric probes.

8. A dialysis machine comprising:
a dialyzer;
a fluid source for supplying fluid to the dialyzer;
a fluid line for communicating the fluid from the fluid source to the dialyzer;
a pump disposed in the fluid line for directing fluid to and/or from the dialyzer;
an electrical sensor comprising:
an electrical fabric probe disposed in the fluid line, the electrical fabric probe comprising non-conductive fabric material and a plurality of conductive strips embedded in the non-conductive fabric material, wherein the plurality of conductive strips are configured for measuring a parameter of the fluid while immersed in the fluid; and
an electrical connector configured to connect the plurality of conductive strips to an electronic controller outside the fluid line; and
the electronic controller, wherein the electronic controller is configured to determine a resistivity and/or a conductivity of the fluid based on the parameter of the fluid measured by the plurality of conductive strips.

9. The dialysis machine of claim 8, wherein the non-conductive fabric material is formed as a non-conductive mesh and the plurality of conductive strips are formed as conductive threads embedded in the non-conductive mesh.

10. The dialysis machine of claim 8, wherein the parameter of the fluid measured by the plurality of conductive strips is a voltage drop corresponding to the fluid.

11. The dialysis machine of claim 8, wherein the electrical sensor further comprises a fluid chamber having a fluid inlet and a fluid outlet, and wherein the electrical sensor is removable from the fluid line.

12. The dialysis machine of claim 11, wherein the electrical fabric probe is disposed within the fluid chamber, and the fluid chamber comprises a first portion and a second portion which are configured to be disassembled to facilitate removal and replacement of the electrical fabric probe disposed within the fluid chamber.

13. The dialysis machine of claim 8, further comprising:
a plurality of additional electrical fabric probes disposed within the fluid line, wherein the plurality of additional electrical fabric probes include second and fourth electrical fabric probes configured to sense temperature and a third electrical fabric probe configured to heat the fluid;
wherein the electronic controller is configured to determine a flow rate of the fluid based on a temperature difference sensed by the second and fourth electrical fabric probes.

14. A method for monitoring a fluid flowing in a fluid line of a dialysis machine during dialysis treatment, the method comprising:
connecting an electrical sensor of the dialysis machine to an electronic controller of the dialysis machine via an electrical connector of the electrical sensor, the electrical sensor comprising an electrical fabric probe disposed in the fluid line, the electrical fabric probe comprising non-conductive fabric material and a plurality of conductive strips embedded in the non-conductive fabric material;
directing the fluid through the fluid line, wherein the plurality of conductive strips of the electrical fabric probe are immersed in the fluid;
measuring a voltage drop across the plurality of conductive strips of the electrical fabric probe; and
determining resistivity and/or conductivity of the fluid based on the measured voltage drop.

15. The method of claim 14, further comprising:
disassembling an enclosure of the electrical sensor and discarding the electrical fabric probe after completion of a dialysis treatment.

16. The method of claim 15, further comprising:
replacing the discarded electrical fabric probe with another electrical fabric probe and reassembling the enclosure of the electrical sensor.

17. The method according to claim 14, wherein the non-conductive fabric material is formed as a non-conductive mesh and the plurality of conductive strips are formed as conductive threads embedded in the non-conductive mesh.

18. The method according to claim 14, wherein the electrical sensor comprises a plurality of additional electrical fabric probes disposed in the fluid line, including a second electrical fabric probe, a third electrical fabric probe, and a fourth electrical fabric probe; and
wherein the method further comprises:
heating the fluid within the electrical sensor using the third electrical fabric probe of the electrical sensor;
sensing temperature of the fluid within the electrical sensor at two different locations using the second and fourth electrical fabric probes of the electrical sensor; and
determining a flow rate of the fluid based on a temperature difference between temperatures sensed by the second and fourth electrical fabric probes.

* * * * *